United States Patent
Kariniemi et al.

(10) Patent No.: US 9,226,839 B1
(45) Date of Patent: Jan. 5, 2016

(54) TORQUE SLEEVE

(71) Applicant: W. L. Gore & Associates, Inc., Newark, DE (US)

(72) Inventors: Thomas E. Kariniemi, Flagstaff, AZ (US); Patrick M. Norris, Bellemont, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 168 days.

(21) Appl. No.: 14/186,561

(22) Filed: Feb. 21, 2014

Related U.S. Application Data

(60) Provisional application No. 61/781,379, filed on Mar. 14, 2013.

(51) Int. Cl.
| | |
|---|---|
| *A61F 2/962* | (2013.01) |
| *A61F 2/82* | (2013.01) |
| *A61F 2/958* | (2013.01) |
| *A61F 2/97* | (2013.01) |

(52) U.S. Cl.
CPC . *A61F 2/962* (2013.01); *A61F 2/82* (2013.01); *A61F 2/958* (2013.01); *A61F 2/97* (2013.01)

(58) Field of Classification Search
CPC ........... A61F 2/95; A61F 2/954; A61F 2/962; A61F 2/966; A61F 2/97; A61F 2002/011; A61F 2002/9517; A61F 2002/9522; A61F 2002/9665
See application file for complete search history.

(56) References Cited

U.S. PATENT DOCUMENTS

| | | | | |
|---|---|---|---|---|
| 5,328,467 | A | 7/1994 | Edwards et al. | |
| 5,647,857 | A * | 7/1997 | Anderson | A61F 2/958 604/160 |
| 5,693,084 | A * | 12/1997 | Chuter | A61B 17/0469 606/194 |
| 6,221,090 | B1 | 4/2001 | Wilson | |
| 6,656,213 | B2 * | 12/2003 | Solem | A61F 2/95 606/108 |
| 6,790,224 | B2 * | 9/2004 | Gerberding | A61F 2/958 623/1.12 |
| 6,827,731 | B2 * | 12/2004 | Armstrong | A61F 2/95 623/1.12 |
| 6,830,575 | B2 * | 12/2004 | Stenzel | A61F 2/95 606/108 |
| 6,899,727 | B2 * | 5/2005 | Armstrong | A61F 2/95 623/1.12 |
| 6,984,242 | B2 * | 1/2006 | Campbell | A61F 2/07 623/1.12 |
| 7,399,311 | B2 * | 7/2008 | Bertolino | A61F 2/95 623/1.11 |
| 7,556,641 | B2 * | 7/2009 | Cully | A61F 2/95 623/1.11 |
| 7,691,138 | B2 * | 4/2010 | Stenzel | A61F 2/95 606/108 |
| 7,753,945 | B2 * | 7/2010 | Bruun | A61F 2/95 606/108 |

(Continued)

*Primary Examiner* — Ryan Severson
(74) *Attorney, Agent, or Firm* — Allan M. Wheatcraft

(57) ABSTRACT

The present disclosure describes an assembly comprising a catheter, an expandable device in a collapsed configuration on the catheter, a first releasable sleeve coaxially covering a proximal portion of the device, and a second releasable sleeve coaxially covering a distal portion of the device, wherein first and second sleeves overlap and are rotatably constrained relative to each other, and wherein the second sleeve is rotatably constrained relative to the catheter. During deployment, rotation of the catheter causes rotation of the second sleeve and the device for angular radial orientation. After deployment, the first sleeve may remain implanted in the patient.

20 Claims, 11 Drawing Sheets

(56) References Cited

U.S. PATENT DOCUMENTS

| | | | |
|---|---|---|---|
| 7,785,360 B2* | 8/2010 | Freitag | A61F 2/95 606/108 |
| 7,963,952 B2* | 6/2011 | Wright, Jr. | A61B 17/22031 604/164.01 |
| 8,012,192 B2 | 9/2011 | Eidenschink et al. | |
| 8,202,309 B2* | 6/2012 | Styrc | A61F 2/95 623/1.11 |
| 8,236,041 B2 | 8/2012 | Sequin et al. | |
| 8,337,542 B2 | 12/2012 | Jantzen et al. | |
| 8,845,712 B2* | 9/2014 | Irwin | A61F 2/966 623/1.11 |
| 9,060,894 B2* | 6/2015 | Wubbeling | A61F 2/95 |
| 2001/0056295 A1* | 12/2001 | Solem | A61F 2/95 623/1.11 |
| 2002/0099431 A1* | 7/2002 | Armstrong | A61F 2/95 623/1.11 |
| 2003/0149466 A1* | 8/2003 | Gerberding | A61F 2/958 623/1.11 |
| 2003/0212410 A1* | 11/2003 | Stenzel | A61F 2/95 606/108 |
| 2004/0024441 A1* | 2/2004 | Bertolino | A61F 2/95 623/1.12 |
| 2004/0073286 A1* | 4/2004 | Armstrong | A61F 2/95 623/1.12 |
| 2004/0122503 A1* | 6/2004 | Campbell | A61F 2/07 623/1.12 |
| 2004/0143315 A1* | 7/2004 | Bruun | A61F 2/95 623/1.11 |
| 2004/0249433 A1* | 12/2004 | Freitag | A61F 2/95 623/1.11 |
| 2005/0033402 A1* | 2/2005 | Cully | A61F 2/95 623/1.11 |
| 2005/0080430 A1* | 4/2005 | Wright | A61B 17/22031 606/108 |
| 2005/0096724 A1* | 5/2005 | Stenzel | A61F 2/95 623/1.11 |
| 2008/0114436 A1 | 5/2008 | Dieck et al. | |
| 2009/0182411 A1* | 7/2009 | Irwin | A61F 2/966 623/1.12 |
| 2009/0299449 A1* | 12/2009 | Styrc | A61F 2/95 623/1.11 |
| 2011/0087318 A1 | 4/2011 | Daugherty et al. | |
| 2011/0208292 A1* | 8/2011 | Von Oepen | A61F 2/97 623/1.23 |
| 2012/0022630 A1* | 1/2012 | Wubbeling | A61F 2/95 623/1.11 |
| 2012/0130475 A1* | 5/2012 | Shaw | A61F 2/97 623/1.12 |
| 2013/0296877 A1* | 11/2013 | Irwin | A61F 2/966 606/108 |
| 2014/0046430 A1* | 2/2014 | Shaw | A61F 2/97 623/1.12 |
| 2014/0142681 A1* | 5/2014 | Norris | A61F 2/97 623/1.12 |

* cited by examiner

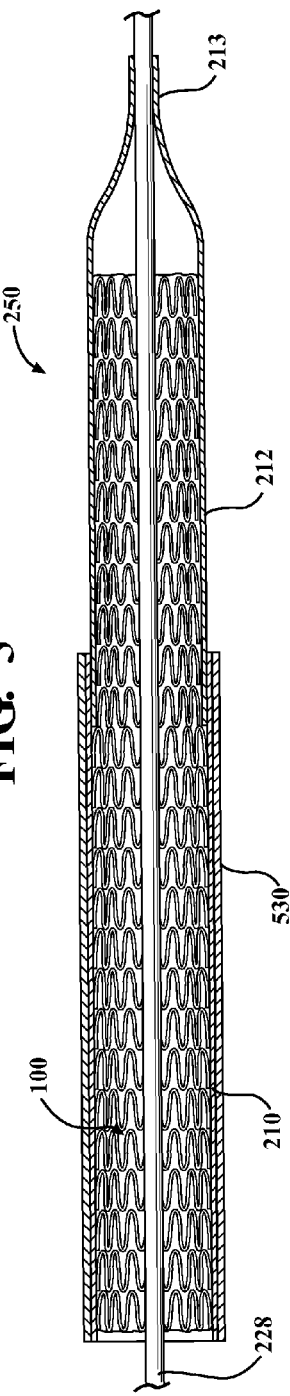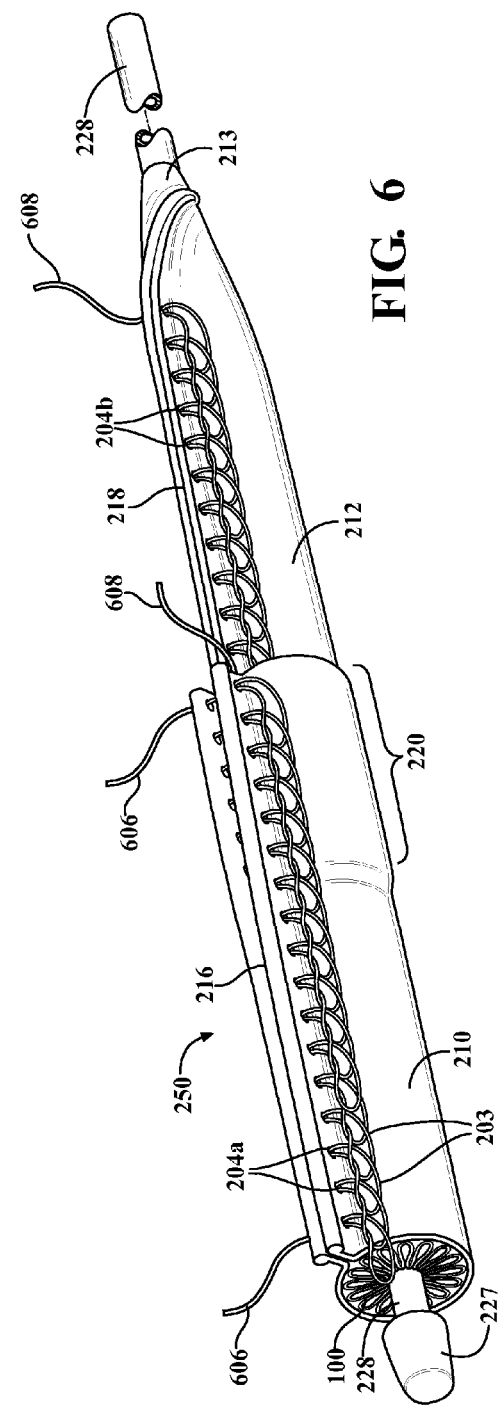

TORQUE SLEEVE

FIELD

The present disclosure relates generally to the remote orientation and deployment of implantable medical devices.

BACKGROUND

Medical devices are frequently used to treat the anatomy of patients. Such devices can be permanently or semi-permanently implanted in the anatomy to provide treatment to the patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and delivered to a treatment site using a catheter. Common types of expandable devices include stents and stent-grafts.

Expandable devices such as stents or stent-grafts are used in a variety of places in the human body to repair aneurysms and to support various anatomical lumens, such as blood vessels, respiratory ducts, gastrointestinal ducts, and the like. Expandable devices may have a reduced diameter when in a collapsed configuration, and they may be expanded once located at the treatment site in the patient. Expandable devices can be constrained in the collapsed configuration with a releasable sleeve to facilitate transport to the treatment site.

Although delivery of an expandable device to a treatment site in a patient may be relatively straightforward, angular radial orientation of the device during deployment may be more problematic. For example, with conventional catheter delivery systems, an expandable device is rotated within the body lumen by applying torque at the proximal end of the catheter outside the patient. However, rotation of the catheter may not result in the desired rotational positioning of the medical device, because the torque applied to the catheter may not fully transfer to a rotation of the device.

As such, there is a need for medical device delivery systems, assemblies and methods that facilitate the angular radial orientation of medical devices during deployment at a treatment site.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein like numerals denote like elements and wherein:

FIG. 5 illustrates a longitudinal cross sectional view of another embodiment of an assembly comprising an expandable medical device constrained in a collapsed configuration in accordance with the present disclosure;

FIG. 6 illustrates a perspective view of another embodiment of an assembly in accordance with the present disclosure;

DETAILED DESCRIPTION OF THE ILLUSTRATED EMBODIMENTS

Figure 1:
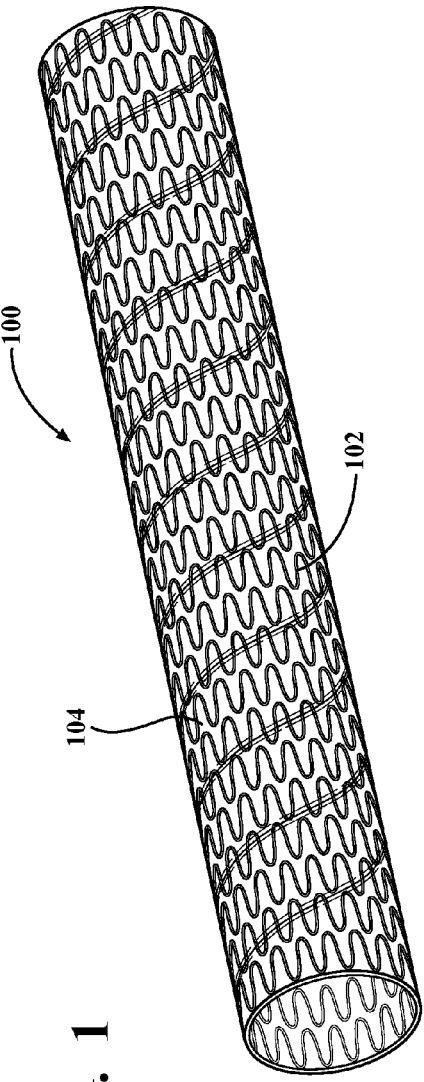
FIG. 1 illustrates a perspective view of an embodiment of an expandable medical device in an expanded configuration in accordance with the present disclosure.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

With that said, and as will be described in more detail herein, various embodiments of the present disclosure generally comprise medical device assemblies configured for the deployment and angular radial orientation of an expandable medical device in a patient.

As used herein, "proximal" indicates a position closer to the heart of the patient, or to a portion of a device that, when implanted, is closer to the heart of the patient than another portion of the device. "Distal" indicates a position farther from the heart of the patient, or to a portion of a device that, when implanted, is farther from the heart of the patient than another portion of the device. Implanted devices having tubular or rod-like shape comprise a distal end, a distal portion, a medial portion, a proximal portion, and a proximal end moving from the end farthest from the heart to the end closest to the heart.

With further regard to the terms proximal and distal, and because the present disclosure is not limited to peripheral and/or central approaches, this disclosure should not be narrowly construed with respect to these terms. Rather, the devices and method described herein can be altered and/or adjusted relative to the anatomy of a patient.

As used herein, a "catheter" is any device suitable for passage through the vasculature to a treatment site. For example, a delivery catheter transports various devices to the treatment site, including, for example, medical devices, tools, lights, and/or any other suitable therapeutic devices. A device may be constrained on an end of a catheter such that the device can be inserted into the vasculature of the patient and directed to a treatment site by manipulation of the end of the catheter residing outside the patient. A catheter can have any cross-sectional shape including, for example, a circular shape, an oval shape, a triangular shape, a square shape, a polygon shape, a uniform shape, or a random shape.

As used herein, "devices" can include, for example, expandable devices such as stents, grafts, stent-grafts and bifurcated stents, filters, valves, occluders, markers, mapping devices, therapeutic agent delivery devices, prostheses, pumps, bandages and other implants.

An "expandable device" can include, for example, any device suitable for delivery to the treatment site at a delivery diameter and capable of dilation from the diameter of the delivery profile, through a range of intermediary diameters, up to a maximal, pre-determined functional diameter. Such expandable devices can include an endoluminal prosthesis, such as for example, stents, grafts, and stent-grafts.

As used herein, the term "constrain" means: (i) to limit expansion, occurring either through self-expansion or expansion assisted by a device, of the diameter of an expandable implant; or (ii) to cover or surround, but not otherwise restrain, an expandable implant (e.g., for storage or biocompatibility reasons and/or to provide protection to the expandable implant and/or the vasculature).

As used herein, an "assembly" can include, for example, a combination of an implantable device, such as a stent, and a delivery device, such as a catheter.

Assemblies in accordance with the present disclosure comprise a catheter, an expandable device, and first and second sleeves constraining the expandable device in a collapsed configuration on an end of the catheter. In various embodiments, the two sleeves overlap and are rotationally constrained relative to each other, with one sleeve rotatably constrained relative to the catheter. The rotational constraint between the first and second sleeves, along with the rotational constraint between one of the sleeves and the catheter, allow the clinician to rotate the device by applying torque to the end of the catheter residing outside the patient. The expandable device may be further constrained by one or more primary sleeves that, when released, allow for the partial expansion of portions of the device to a diameter determined by at least one inner secondary sleeve. Various embodiments of the present disclosure further comprise a method for the deployment and angular radial orientation of an expandable device in a patient, wherein a first sleeve is partially or fully released to deploy at least a proximal portion of the device, leaving a second sleeve rotationally constrained to the first sleeve and to the catheter, such that rotation of the catheter by the practitioner causes rotation of the second sleeve and the expandable device. The second sleeve, once released, is removable along with the catheter from the patient.

With reference now to FIG. 1, an expandable device 100 in accordance with the present disclosure is illustrated in an expanded configuration. Expandable device 100 is a stent-graft comprising a stent 102 and a graft member 104. In various embodiments, graft member 104 is affixed to the outside surface of stent 102 such that once deployed, graft member 104 is placed into contact with a vessel wall. In other embodiments, graft member 104 is affixed to the inside surface of stent 102 such that once deployed, graft member 104 is not in contact with a vessel wall.

In various embodiments, the stent 102 can comprise, for example, a plurality of stent rings, cut tubes, wound wires (or ribbons) or flat patterned sheets rolled into a tubular form. Stent rings may be operatively coupled to one another with a wire. Stent components can be formed from metallic, polymeric or natural materials and can comprise conventional medical grade materials such as for example nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as iron alloys, stainless steels, cobalt-chromium alloys, nitinol, and the like; and biologically derived materials such as bovine arteries/veins, pericardium and collagen. Stent components can also comprise bioresorbable organic materials such as poly(amino acids), poly(anhydrides), poly(caprolactones), poly(lactic/glycolic acid) polymers, poly(hydroxybutyrates) and poly(orthoesters).

In various embodiments, the graft member 104 can comprise, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for graft material can include high strength polymer fibers such as ultra-high molecular weight polyethylene fibers (e.g., Spectra®, Dyneema Purity®, etc.) or aramid fibers (e.g., Technora®, etc.).

In various embodiments, expandable device 100 can comprise a radially collapsed configuration suitable for delivery to the treatment area of the vasculature of a patient. Expandable device 100 may be constrained in a radially collapsed configuration and mounted onto a delivery device, such as a catheter, to form an assembly.

In various embodiments, expandable device 100 can comprise a radially expanded configuration suitable for implant in the treatment area of a patient's vasculature. In the expanded configuration, the diameter of expandable device 100 may be approximately the same as the vessel to be repaired or slightly larger than the vessel to be treated to provide a traction fit within the vessel.

In various embodiments, expandable device 100 may be a self-expanding medical device. Such devices dilate from a radially collapsed configuration to a radially expanded configuration when unconstrained.

In various embodiments, expandable device 100 may be balloon-expandable with the assistance of a secondary device such as, for example, a balloon catheter or spring mechanism.

In various embodiments, expandable device 100 is constrained by one or more "sleeves" covering the expandable device. One of more sleeves can circumferentially surround a device and constrain the device toward a collapsed configuration, in which the diameter is less than the diameter of an unconstrained device. In various embodiments, a sleeve can constrain an expandable device to any intermediate diameter between the fully expanded diameter and the fully collapsed diameter.

Figure 2:
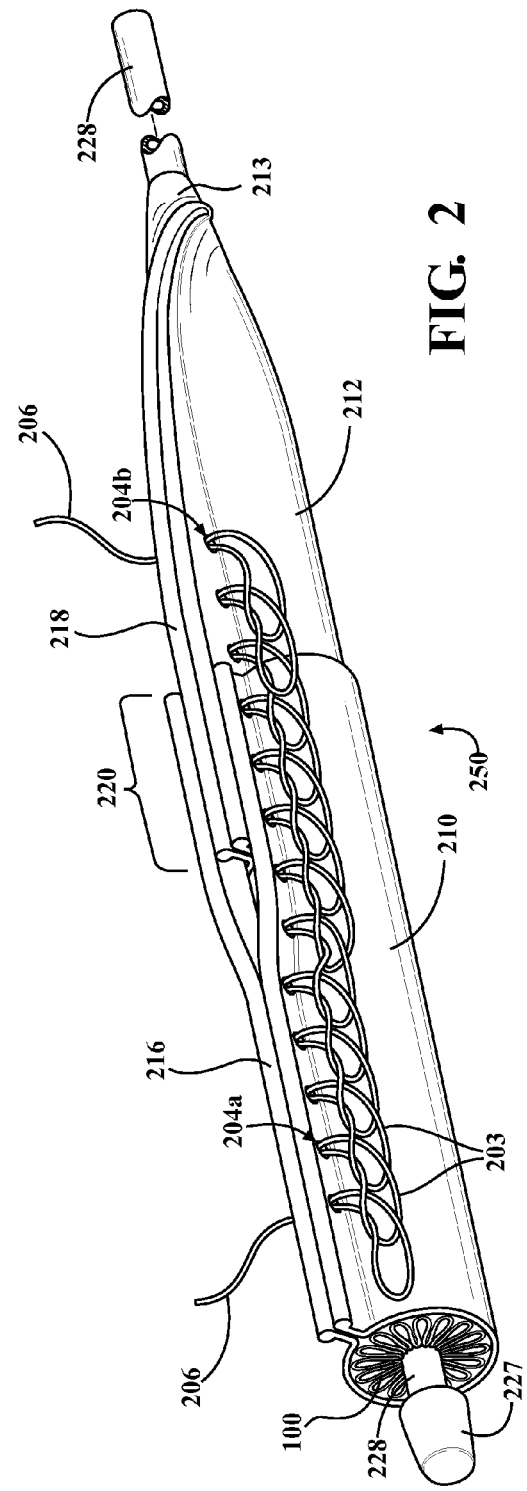
FIG. 2 illustrates a perspective view of an embodiment of an assembly comprising an expandable medical device constrained in a collapsed configuration in accordance with the present disclosure.

Referring now to FIG. 2, an embodiment of an assembly 250 in accordance with the present disclosure is illustrated. The assembly 250 comprises a catheter 228, a proximal barrier 227, and an expandable device 100 disposed in a collapsed configuration on an end of catheter 228 by both a first releasable sleeve 210 and a second releasable sleeve 212. First sleeve 210 is covering and constraining a proximal portion of the device 100, whereas the second sleeve 212 is covering and constraining a distal portion of the device 100. Together, the two releasable sleeves constrain the entire length of the device 100. The two coaxially oriented sleeves overlap in overlap zone 220. In the embodiment illustrated, a distal portion of the first sleeve 210 overlaps a proximal portion of the second sleeve 212. In various other embodiments, the second sleeve 212 may overlap a portion of the first sleeve 210. With the first sleeve 210 overlapping, and unobstructed by, the second sleeve 212, the first sleeve 210 may be released from the device first, as part of a multistage deployment procedure. The overlap zone 220 may be any length. The overlap zone 220 can comprise relatively minor portions of each sleeve, (e.g., 1-50% of each sleeve). In other embodiments, the overlap zone 220 can comprise relatively major portions of each sleeve, (e.g., 50-99% of each sleeve). The first releasable sleeve 210 is rotatably constrained relative to the second releasable sleeve 212 by at least one of friction, dissolvable adhesive, temperature-activated adhesive or, as illustrated in FIG. 2, stitching, in the overlap zone 220. While the illustrative embodiment is described as comprising two partially overlapping tubular sleeves, sleeves of any non-tubular shape that correspond to an underlying expandable device, or that are otherwise appropriately shaped for a given application, are also within the scope of the present disclosure.

In the assembly 250, two separate flat sheets of material are wrapped circumferentially around portions of the device 100 to form each of the two tubular sleeves. First sleeve 210 and second sleeve 212 each include a pair of opposing and substantially parallel edges that are joinable by a coupling member 206 threaded or woven through rows of openings 204a and 204b disposed along each edge. The openings 204a on first sleeve 210 and the openings 204b on second sleeve 212 are disposed along a common longitudinal axis, and lined up in the overlap zone 220, such that a single, relatively linear stitching of the coupling member 206 can be used to close both sleeves and constrain the entire length of the device 100.

In various embodiments, a sleeve can comprise materials similar to those used to form graft members. A sleeve can be made of any suitable material, including for example, a fluoropolymer such as ePTFE. Alternatively, or in combination with a fluoropolymer, the sleeve can be formed of biocompatible materials, such as polymers, which can include fillers such as metals, carbon fibers, Dacron, glass fibers or ceramics. Such polymers can include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalates, polypropylenes, polyethylenes, polyurethanes, polyolefins, polyvinyls, polymethylacetates, polyamides, naphthalane dicarboxylene derivatives, and natural silk can be included in the sleeve.

In various embodiments, the coupling member 206 can comprise a woven fiber or a monofilament fiber. Any type of string, cord, thread, fiber, or wire capable of constraining a sleeve around an expandable device is within the scope of the present disclosure. For example, the coupling member can comprise ePTFE fiber such as (KORETEK®), sutures of polyethers such as polyethylene terephthalate (DACRON® or MYLAR®) or polyacrylamides such as KEVLAR®. The coupling member 206 may alternatively comprise a metal wire made from nitinol, stainless steel, or gold.

With continued reference to FIG. 2, first sleeve 210 comprises a first releasable seam 216, and second sleeve 212 comprises a second releasable seam 218, secured by the weaving of a coupling member 206 through the rows of openings 204a and 204b. First releasable seam 216 and second releasable seam 218 are aligned into one longitudinally contiguous releasable seam, with an end of the second seam 218 fit inside an end of first seam 216, as part of the overlap zone 220. In this embodiment, the two sleeves are rotatably constrained relative to each other by the stitching running through both sleeves in overlap zone 220. In other embodiments, the two partially overlapping sleeves may be rotatably constrained to each other by a dissolvable or temperature-activated adhesive. Within the overlap zone 220, the stitching is woven through all four (4) layers of sheet material. The threading or weave of coupling member 206 can comprise any variation of stitching, such as for example a chain stitch comprising individual slip knots or loops 203. The second sleeve 212 is rotatably constrained relative to the catheter 228 at region 213 by any temporary or permanent fixation, such as, for example, a dissolvable, temperature-sensitive, or permanent adhesive. In various embodiments, the second sleeve 212 may be rotatably constrained to the catheter 228 by compressing a distal portion of sleeve 212 around the catheter and optionally bonding. In various embodiments, a distal portion of the second sleeve 212 may be secured to a distal barrier mounted on the catheter 228, rather than directly to the catheter 228.

Still referring to FIG. 2, an end of the coupling member 206 may be of sufficient length to form a remote pull line used for tensioning and deployment of the device 100, while the other end of coupling member 206 may be affixed to the second sleeve 212 or to the catheter 228. Coupling member(s), and/or the remote pull line(s) to which they are attached, may be routed outside the patient through a lumen disposed in the catheter 228. When the device 100 is at the treatment site of the patient, the coupling member 206 can be disengaged from the sleeves by tensioning the coupling member(s) and/or remote pull line(s) from outside of the body of the patient, which allows the sleeves to open and the expandable device 100 to expand. Tensioning, actuation and displacement of the coupling member 206 from the openings 204a and 204b allows the first releasable sleeve 210 and second releasable sleeve 212 to open along the releasable seams 216 and 218, respectively, and for the device 100 to expand from a compacted state. "Deployment" refers to the actuation of the device at the treatment site, such as for example, the release of a releasable sleeve on a self-expanding device to allow the device to expand. The deployment process may be in stages, such as for example, release of first sleeve 210 in a first stage and release of second sleeve 212 in a second stage.

Figure 3:
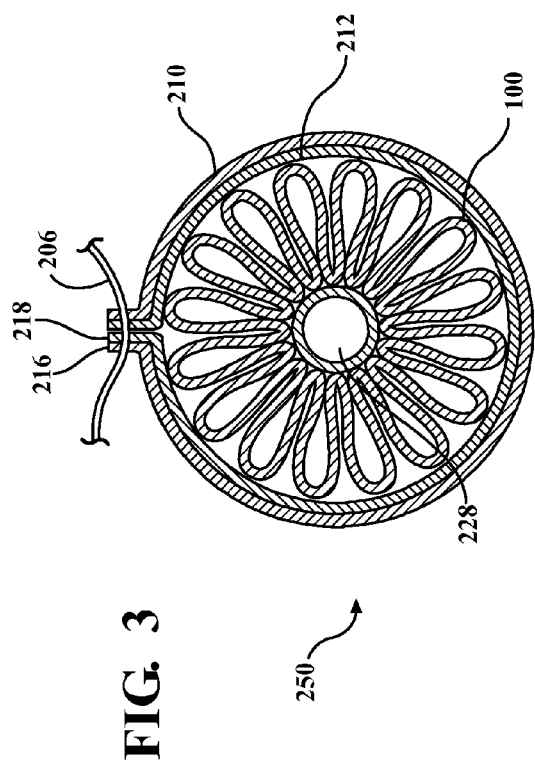
FIG. 3 illustrates a cross sectional view of an embodiment of an assembly comprising an expandable medical device constrained in a collapsed configuration in accordance with the present disclosure.

Referring now to FIG. 3, an axial cross-section of an embodiment of an assembly in accordance with the present disclosure is illustrated. For this view, the assembly 250 is axially cross-sectioned within the overlap zone 220 (see FIG. 2). FIG. 3 illustrates the end-on view of the distal portion of the cross-sectioned device. As shown, assembly 250 comprises first sleeve 210 wrapped circumferentially over second sleeve 212, wherein both sleeves 210 and 212 constrain portions of the expandable device 100 in a compacted configuration on the catheter 228. Both sleeves 210 and 212 extend around the device 100, with each set of opposing edges releasably secured together by coupling member 206 into releasable seams 216 and 218.

Figure 4:
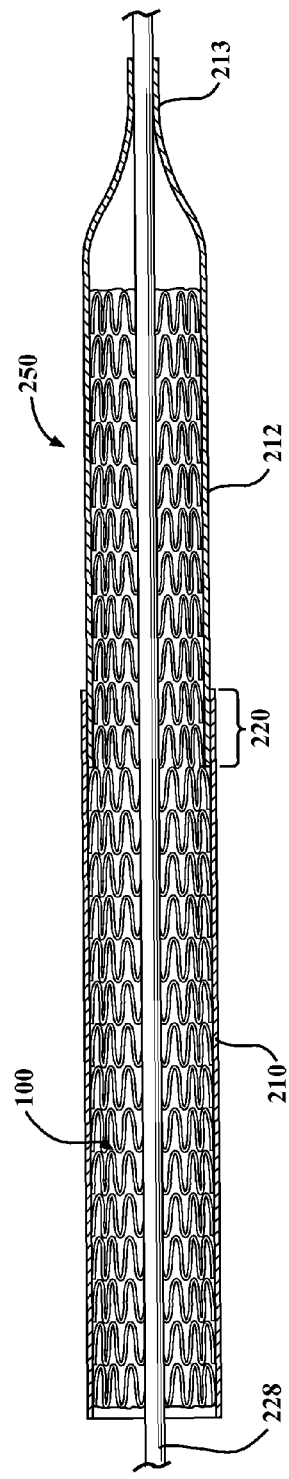
FIG. 4 illustrates a longitudinal cross sectional view of an embodiment of an assembly comprising an expandable medical device constrained in a collapsed configuration in accordance with the present disclosure.

Referring now to FIG. 4, a longitudinal cross-section of an embodiment of an assembly 250 in accordance with the present disclosure is illustrated. First releasable sleeve 210 constrains a proximal portion of the device 100 in a reduced diameter on the catheter 228. Second releasable sleeve 212 constrains a distal portion of the device 100 in a reduced diameter on the catheter 228. The adjacent sleeves overlap in overlap zone 220, the length of which may be determined by the nature of the medical treatment at hand, the type of device 100, and/or the patient's vasculature, among other factors. A distal portion of first sleeve 210 overlaps a proximal portion of second sleeve 212 in the overlap zone 220. In other embodiments the overlap may be opposite. Second sleeve 212 tapers in diameter at its distal end to a portion affixed to the catheter 228. As discussed above, second sleeve 212 is rotatably constrained relative to the catheter 228 at region 213 by any permanent or temporary fixation. In various other embodiments, the second sleeve 212 may be affixed to a distal barrier (not illustrated) mounted on the catheter 228, rather than directly to the catheter 228.

Referring now to the embodiment of FIG. 5, assembly 250 comprises three sleeves. Secondary sleeve 210 and second primary sleeve 212 constrain proximal and distal portions, respectively, of device 100 on catheter 228. The second primary sleeve 212 may constrain the distal portion of the device 100 to a fully collapsed delivery diameter, whereas secondary sleeve 210 may constrain the proximal portion of the device 100 to a diameter between the fully collapsed delivery diameter and the fully expanded treatment diameter. In various embodiments, sheet material folding and/or double stitching can be used to impart both primary and secondary sleeve characteristics to a single sleeve. In such embodiments, a single sleeve may be released to a first intermediate diameter, and then fully released to a completely open configuration. In assembly 250, sleeves 210 and 212 partially overlap as illustrated and are rotatably constrained relative to each other as discussed above. The second primary sleeve 212 is rotatably constrained to the catheter at region 213. Additionally, a first primary sleeve 530 is disposed concentric to secondary sleeve 210, substantially encasing it, and constraining the proximal portion of the device 100, and the secondary sleeve 210 underneath, to a collapsed delivery diameter. Two or three separate stitch lines (not illustrated) can be used to secure each of the three sleeves of the assembly 250. For example, a first stitch line may secure only the first primary sleeve 530. A second stitch line may secure both secondary sleeve 210 and second primary sleeve 212, rotatably constraining them to each other. Alternatively, each of said secondary sleeve 210 and second primary sleeve 212 can be secured with separate stitching. With two or three stitch lines securing the three sleeves, device 100 can be deployed in stages, with release of the first primary sleeve 530 preceding either a sequential or a simultaneous release of secondary sleeve 210 and second primary sleeve 212.

Referring now to FIG. 6, another embodiment of an assembly 250 in accordance with the present disclosure is illustrated. The assembly 250 comprises a catheter 228, a proximal barrier 227, and an expandable device 100 constrained into a compacted diameter on an end of catheter 228 by both a first releasable sleeve 210 and a second releasable sleeve 212. The first sleeve 210 constrains a proximal portion of the device 100 whereas the second sleeve 212 constrains a distal portion of the device 100. The two adjacent sleeves overlap in overlap zone 220 having any degree of overlap as required. A distal portion of first releasable sleeve 210 overlaps a proximal portion of second releasable sleeve 212, and although the two sleeves are not stitched together in this embodiment, the first and second sleeves are nonetheless rotatably constrained relative to each other by a frictional fit or by any type of adhesive. Two individual sheets of material are wrapped circumferentially around portions of the device 100 to form each of the two generally tubular sleeves. As previously discussed, each sleeve comprises a pair of opposing and substantially parallel edges that are joinable into a releasable seam. The rows of openings 204a and 204b are configured on each sleeve for securing with separate and distinct first and second coupling members 606 and 608, respectively. First sleeve 210 comprises a first releasable seam 216 and second sleeve 212 comprises a second releasable seam 218. The two releasable seams may be oriented in the same longitudinal axis or they may be rotated from each other. The second releasable seam 218 need not extend the entire length of the second sleeve 212, and in various embodiments, the second sleeve 212 can comprise a tubular proximal end devoid of a seam. Second sleeve 212 is rotatably constrained relative to the catheter 228 by affixation to the catheter 228 (or to a distal barrier mounted on the catheter) at region 213 by any means discussed previously.

Still referring to FIG. 6, first releasable seam 216 is held together by a first coupling member 606 woven through the openings 204a, with one end of the first coupling member 606, or a pull-line attached thereto, extending outside the patient for tensioning and disengagement from first sleeve 210. Tensioning, actuation and displacement of the first coupling member 606 from the openings 204a allows the first sleeve 210 to open along the releasable seam 216 and for a proximal portion of the device 100 to expand, or be available for expansion, from a compacted state. Similarly, second releasable seam 218 is held together by a second coupling member 608 woven through the openings 204b, with one end of the second coupling member 608, or a pull-line attached thereto, extending outside the patient for tensioning and disengagement. Tensioning, actuation and displacement of the second coupling member 608 from the openings 204b allows the second sleeve 212 to open along the second releasable seam 218 and for a distal portion of the device 100 to expand, or be available for expansion, from a compacted state. The coupling members, or the remote pull-lines to which they are attached, may be routed through a lumen in the catheter 228. The proximal end of the second sleeve 212 may not be visible since it is underneath the distal end of the first sleeve 210. Additionally, the second coupling member 608 is partly underneath first sleeve 210 at least for a portion of its length. The most proximal stitches securing the second sleeve 212 may also not be visible since they are underneath first sleeve 210. The other end of the second coupling member 608 may be affixed to the second sleeve 212 or to the catheter 228.

FIGS. 7-10 collectively illustrate an embodiment of a method of deploying an expandable medical device within the lumen of a patient in accordance with the present disclosure.

Figure 7:
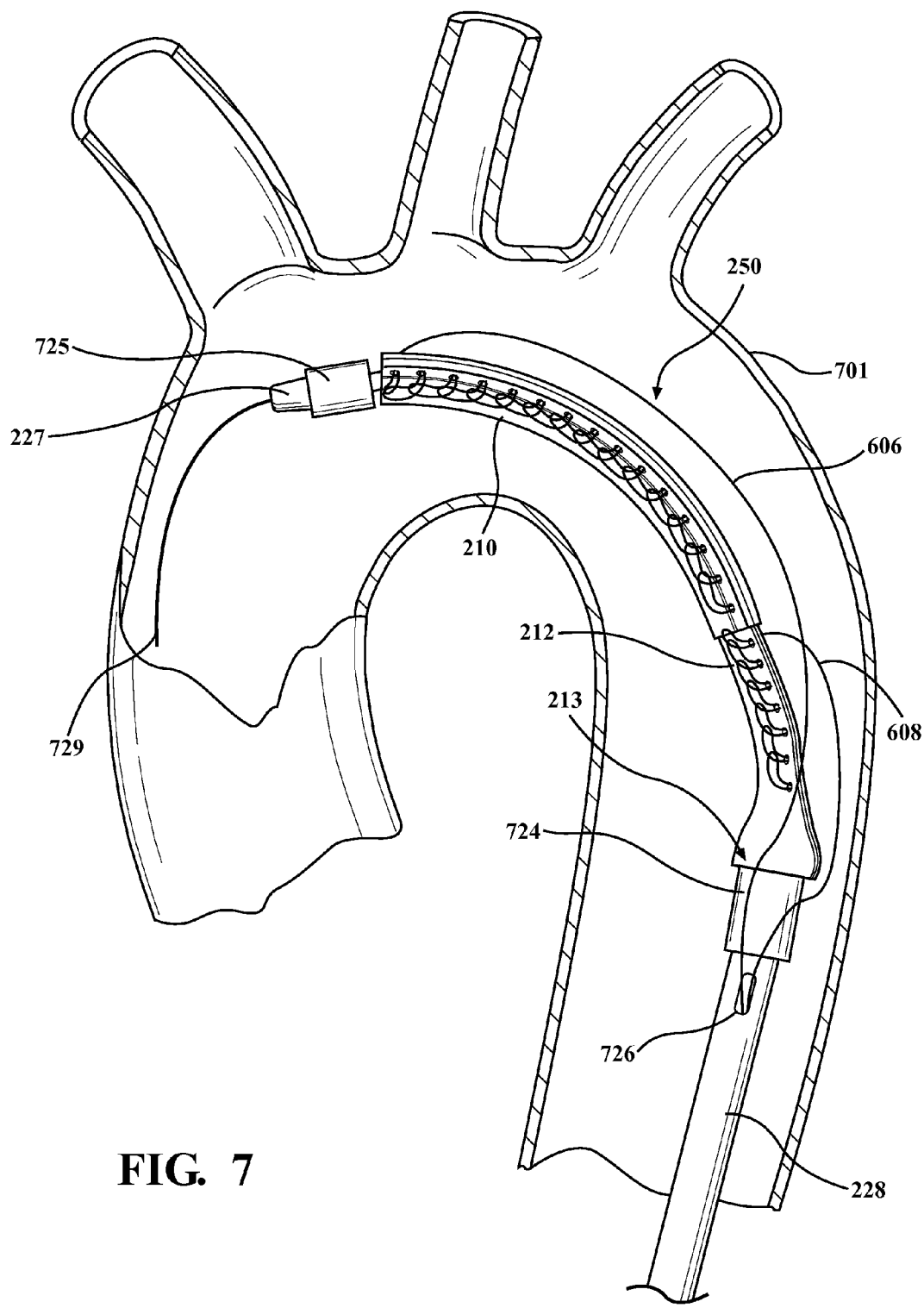
FIGS. 7-10 illustrate steps in the deployment of an expandable device constrained with two sleeves in accordance with the present disclosure.

With reference now to FIG. 7, an assembly 250 is illustrated in a treatment site 701 of a patient. Catheter 228 and guide wire 729 assist in locating the assembly 250 at the treatment site 701 within the vasculature. Leading proximal barriers 227 and 725 may be used on the assembly 250. Assembly 250 comprises a first sleeve 210 and a second sleeve 212 that together constrain proximal and distal portions of an expandable device (possibly not visible constrained under the sleeves, and not illustrated as such). First sleeve 210 is releasably secured around a proximal portion of the expandable device by first coupling member 606, an end of which extends from the proximal end of the stitching on the first sleeve 210 for tensioning and disengagement. Similarly, second sleeve 212 is releasably secured around a distal portion of the expandable device by second coupling member 608, an end of which extends from the proximal end of the stitching on the second sleeve 212 for tensioning and disengagement. The stitching on second sleeve 212 begins at a proximal end of second sleeve 212 underneath a distal portion of first sleeve 210. Both first coupling member 606 and second coupling member 608 may be threaded into portal 726 and through a lumen provided in the catheter 228 to a position outside the patient. The two sleeves are not stitched together in this embodiment, but are nonetheless rotatably constrained relative to each other by virtue of the tight friction fit between them, and/or by a dissolvable and/or temperature-activated adhesive. Additionally, second sleeve 212 is rotatably constrained to a distal barrier 724 mounted on the catheter 228 at region 213 by friction, adhesive, and/or thermal bonding. Once the assembly 250 is positioned at the treatment site 701 as shown in FIG. 7, the expandable device constrained therein is ready for a multistage deployment that includes stages of angular radial orientation as needed.

Figure 8:
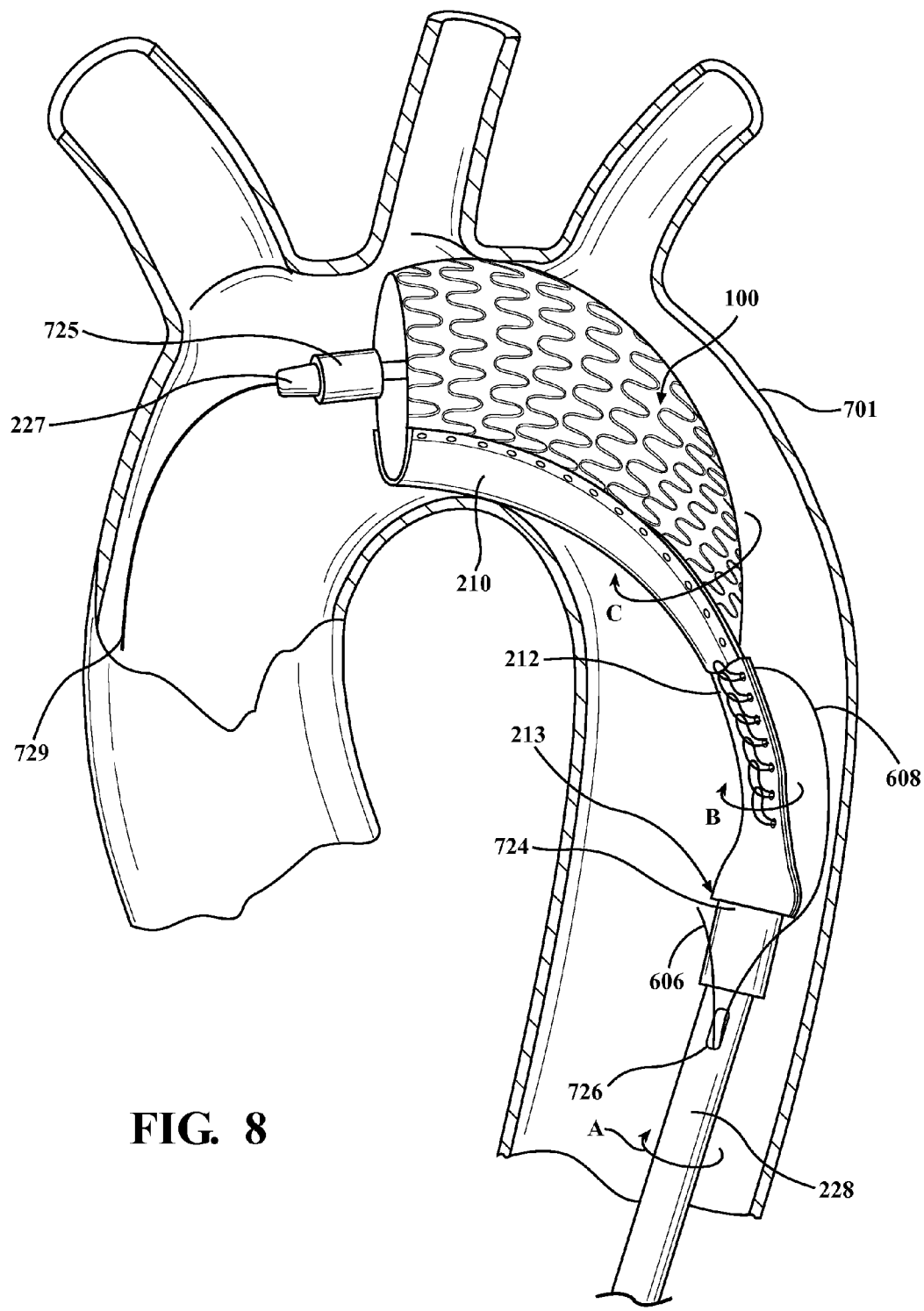

Referring now to FIG. 8, deployment of expandable device 100 comprises tensioning and disengagement of first coupling member 606 from first sleeve 210 to release first sleeve 210. The disengagement of first coupling member 606 can be all at once or in paused increments as needed. In FIG. 8, first coupling member 606 is fully disengaged from first sleeve 210, and the end of the coupling member 606 is ready to be withdrawn completely into portal 726 and out through a lumen disposed in the catheter 228. A proximal portion of expandable device 100 is expanded, which may be the result of self-expansion and/or balloon-assisted expansion. The assembly can be oriented in any rotational configuration as needed so that the first sleeve 210 can be left behind in a particular location in the lumen. Depending on the diameter to which a proximal portion of the device 100 is expanded, and/or the nature of the particular treatment site 701, the proximal end of the device 100 may be more or less anchored into the vasculature. Rotation "A" of the end of the catheter 228 causes rotation "B" of the secured second sleeve 212, which in turn causes rotation "C" of the partially expanded device 100, because the sleeves 210 and 212 remain overlapped and rotatably constrained relative to each other and the second sleeve 212 remains rotatably constrained to the catheter 228. The partially expanded device 100 may be rotated as needed to achieve the desired angular radial orientation.

In various embodiments, the expandable device 100 can comprise at least one target portion located on the surface of the device. In various embodiments, the target portion or portions can comprise side branch fenestrations. Side branch fenestrations allow for branching devices, such as branching stent-grafts, to be connected to, and in communication with, the expandable device. Thus, angular axial orientation may be used to properly align features such as side branch fenestrations in the vasculature. In the case of balloon-assisted expansion of the proximal portion of device 100, rotating and manual expanding can be employed in any order as needed to orient the device 100 and expand the proximal portion. In various embodiments, the proximal portion of the device can be further optionally expanded as needed at any time while deploying the expandable device.

Figure 9:
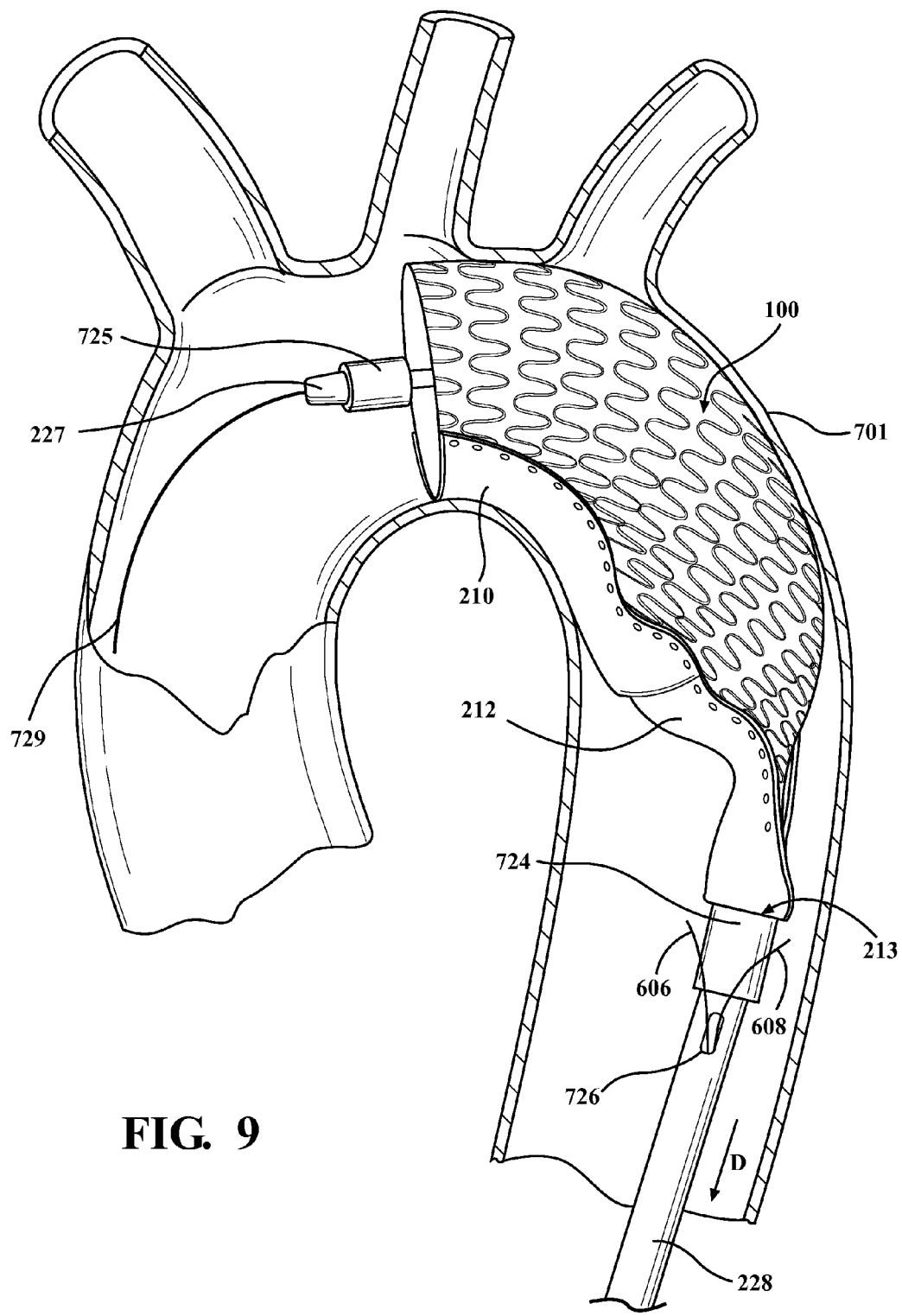

Now referring to FIG. 9, deployment of expandable device 100 at the treatment site 701 further comprises release of the second sleeve 212, which previously constrained a distal portion of the device 100. Release of the second sleeve 212 may be all at once or partitioned in paused increments as needed. Second sleeve 212 may be released by the tensioning and disengagement of the second coupling member 608 from a position outside the patient. With the stitching fully disengaged from second sleeve 212, the end of second coupling member 608 may be fully withdrawn inside portal 726 and out from the patient through a lumen disposed in the catheter 228. In various embodiments, the distal portion of the device can be further optionally expanded as needed at any time while deploying the expandable device. First sleeve 210 and second sleeve 212, although both fully released, may remain adhered together by a dissolvable or temperature-activated adhesive that has not yet dissolved or has not yet been temperature deactivated.

With further reference to FIG. 9, the distal end of the device 100 may remain at least partially constrained inside portion of a tubular distal end of the second sleeve 212 not having a releasable seam. The remaining end of the device 100 may be released by withdrawal of the catheter 228 as indicated by "D." Since the second sleeve 212 remains attached to the catheter 228 at region 213, second sleeve 212 may be withdrawn along with catheter 228.

Figure 10:
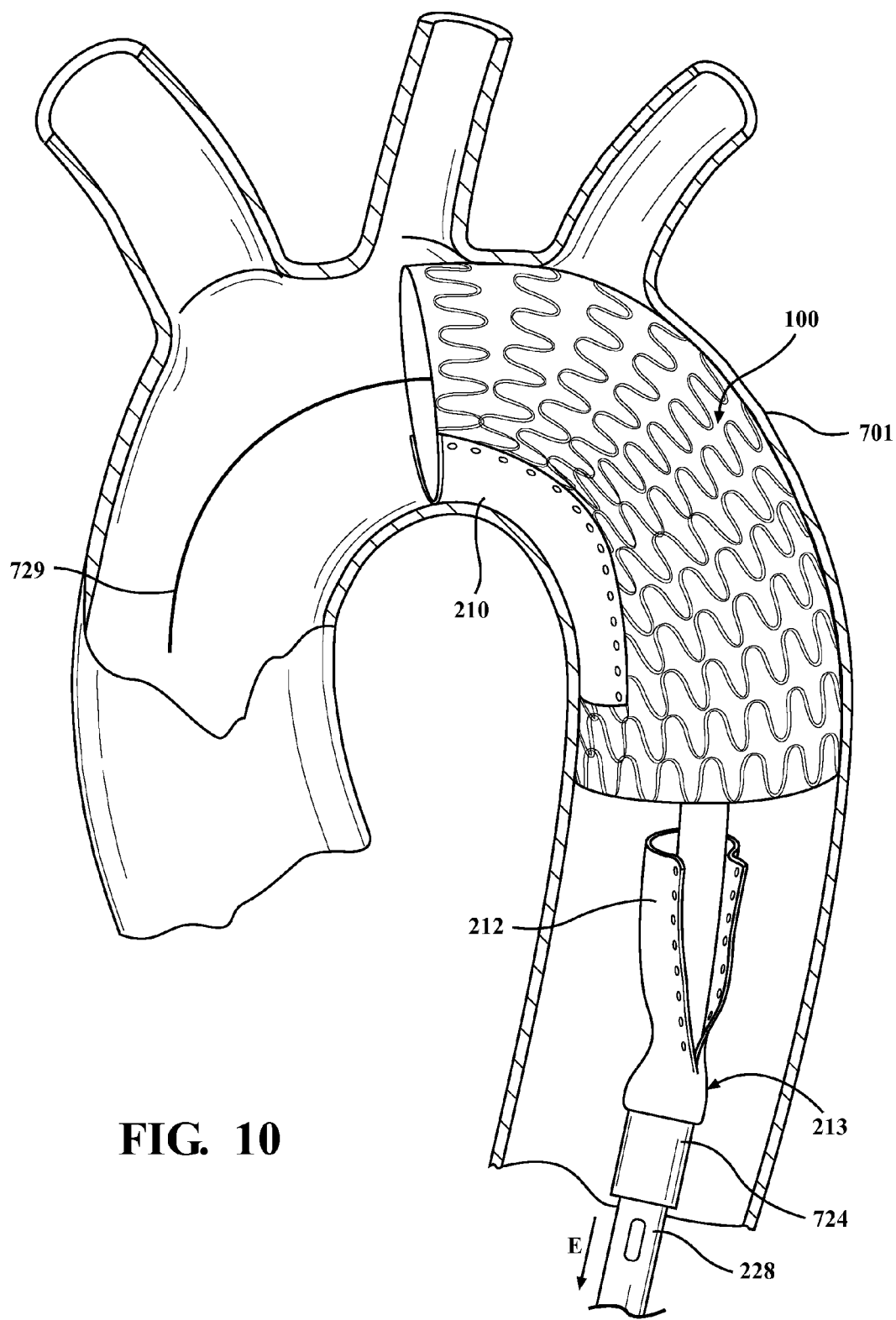

FIG. 10 illustrates the fully deployed and angularly oriented device 100 at the treatment site 701 in the patient. The first released sleeve 210 is left behind. The released second sleeve 212, affixed to the distal barrier 724 of catheter 228 at region 213, may be removed from the proximal end of the device 100 upon withdrawal of the catheter 228 in direction "E." The two coupling members that previously constrained first sleeve 210 and second sleeve 212 have been completely withdrawn through the catheter 228 and are no longer visible. The remaining guide wire 729 can be removed from the patient to complete the deployment and angular radial orientation procedure.

FIGS. 11-14 collectively illustrate another embodiment of a method of deployment of an expandable medical device within the lumen of a patient in accordance with the present disclosure. In this embodiment, the assembly comprises three distinct sleeves.

Figure 11:
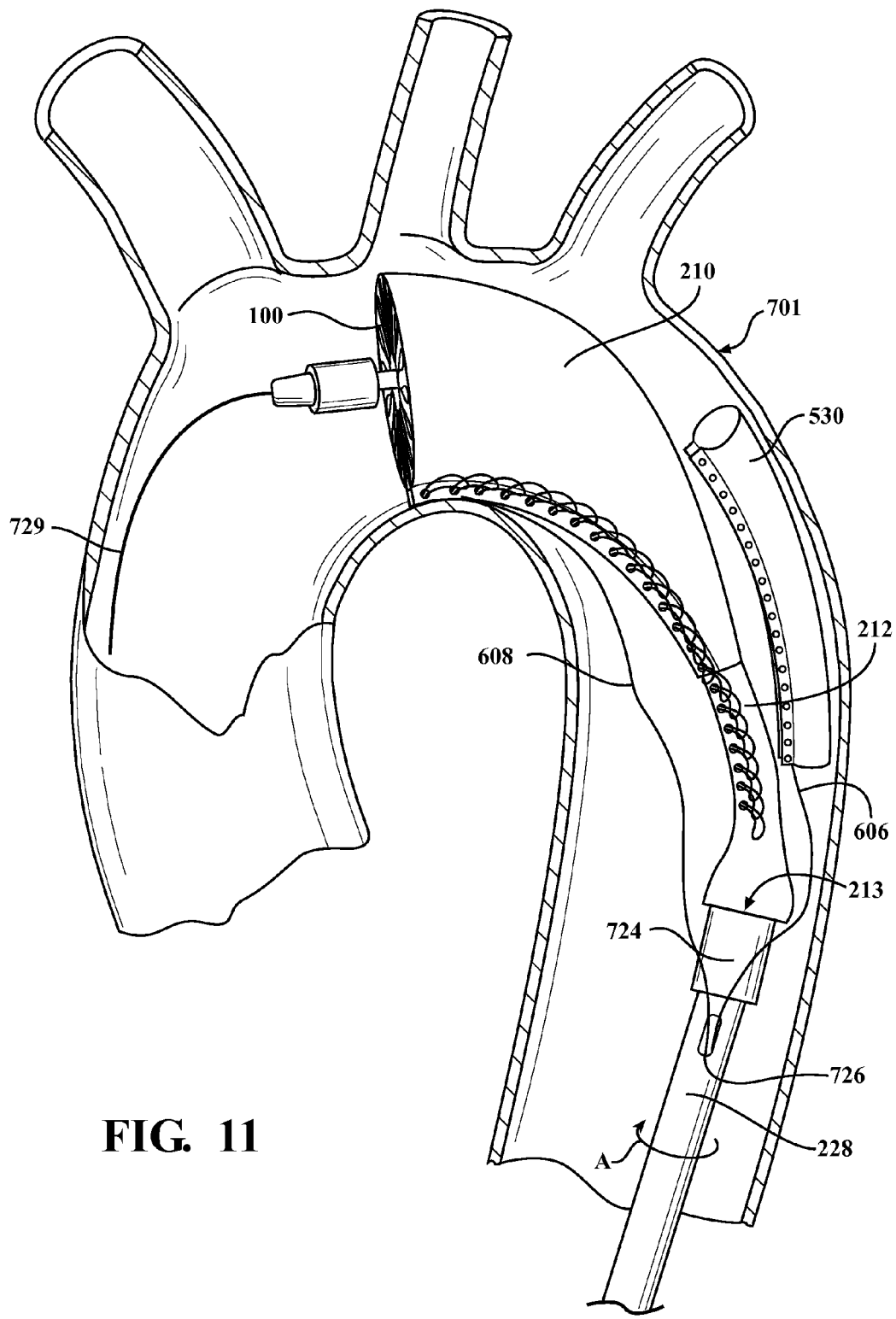
FIGS. 11-14 illustrate steps in the deployment of an expandable device constrained with three sleeves in accordance with the present disclosure.

Referring now to FIG. 11, partial deployment of an expandable device 100 at the treatment site 701 of the patient comprises a release of a first primary sleeve 530 from a proximal portion of the device 100. Release of first primary sleeve 530 may be all at once, or in increments as required. As illustrated, the first primary sleeve 530 is entirely freed from the expandable device 100, allowing a proximal portion of the device 100 to self-expand, or be manually expanded, to an intermediate diameter determined by the size and nature of the remaining secondary sleeve 210. As such, the proximal portion of the expandable device 100 is held from further expansion by the presence of the secondary sleeve 210. An end of the first coupling member 606 may remain attached to the first primary sleeve 530, wherein it can be used as a tether for removal of the first primary sleeve 530 from the patient. As discussed in an alternative embodiment below, the first primary sleeve 530 may also be left in the patient post deployment. With the first primary sleeve 530 released, a proximal portion of the device 100 may self-expand or be manually expanded to an expanded diameter. Rotation "A" of an end of the catheter 228 causes rotation of the device 100 for angular radial orientation as needed. The torque applied to the catheter 228 causes rotation of the device 100 because the secondary sleeve 210 and the second primary sleeve 212 remain stitched together and rotationally constrained to each other, and the second primary sleeve 212 remains rotationally constrained to the catheter 228. A single stitching from a second coupling member 608 secures both the secondary sleeve 210 and the second primary sleeve 212 and secures the sleeves to each other. The second primary sleeve 212 is rotationally constrained to a distal barrier 724 mounted on, and rotationally constrained to, the catheter 228. In other embodiments, the second primary sleeve 212 may be attached directly to the catheter 228. The first coupling member 606 and second coupling member 608 may be threaded into a portal 726 and routed through a lumen disposed in the catheter 228. In various other embodiments, two separate coupling members can be used to secure secondary sleeve 210 and second primary sleeve 212 and all three coupling members can be threaded through a portal such as 726 and into the catheter 228.

With continued reference to FIG. 11, the desired intermediate diameter at which the proximal portion of the device 100 remains constrained depends on a number of factors considered in the design and manufacture of the assembly 250, including the medical procedure to be performed and the nature of the patient's vasculature. In this regard, the secondary sleeve 210 may constrain the proximal portion of the device 100 to any intermediate diameter required. Tensioning and disengagement of the second coupling member 608 unstitches the single stitch line to release both the remaining secondary sleeve 210 and second primary sleeve 212.

Figure 12:
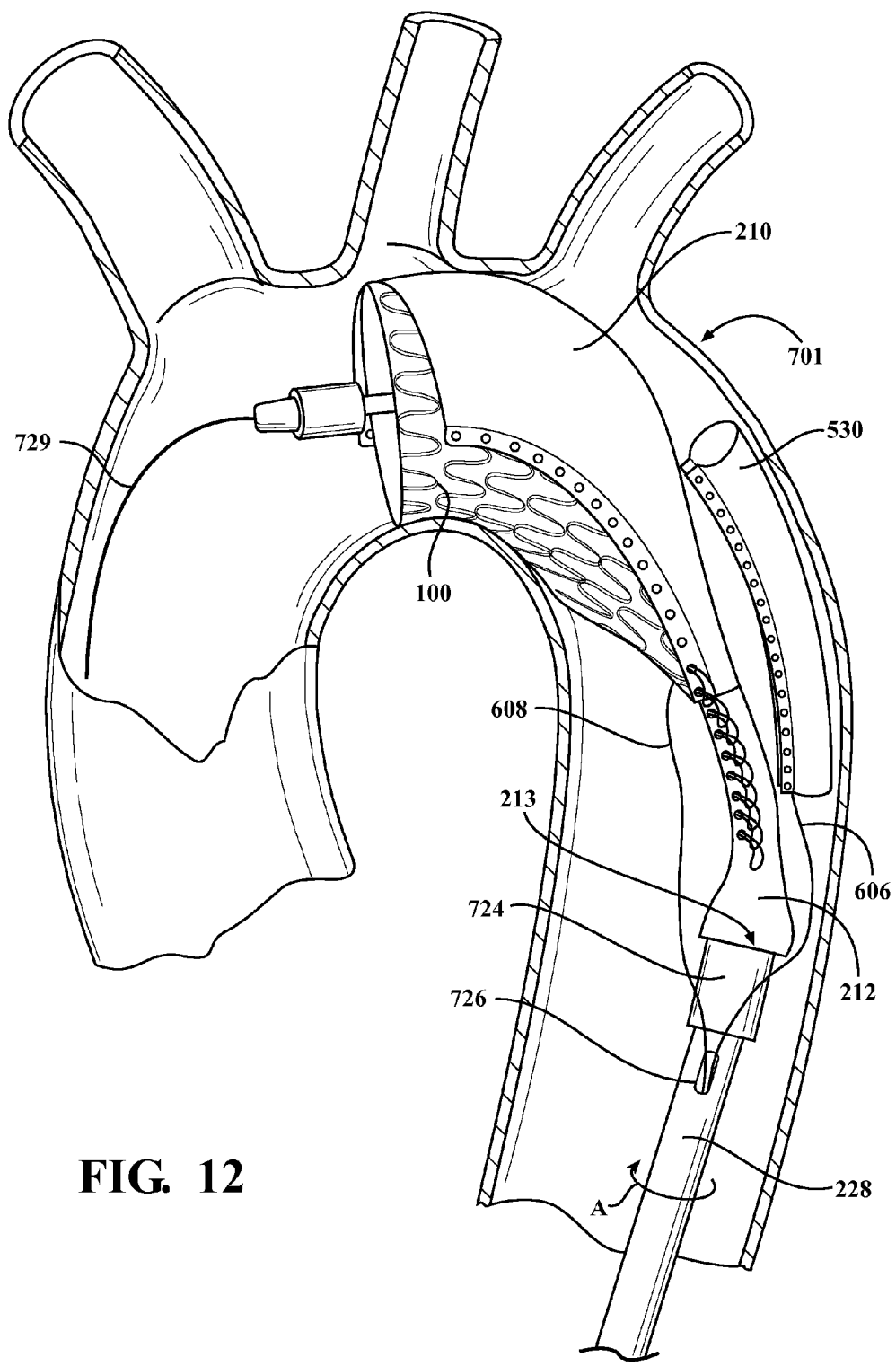

With reference now to FIG. 12, deployment of expandable device 100 at the treatment site 701 further comprises release of the secondary sleeve 210, which previously constrained a proximal portion of the device 100 to an intermediate diameter. As with any of the sleeves, release of the secondary sleeve 210 may be all at once or incremental as needed. Secondary sleeve 210 may be released by the tensioning and disengagement of the second coupling member 608 from a position outside the patient. With the secondary sleeve 210 and second primary sleeve 212 secured with a single coupling member 608, continued tensioning of the second coupling member 608 will disengage the second coupling member 608 from the second primary sleeve 212 and release it after secondary sleeve 210. Disengagement of the second coupling member 608 from the two sleeves may be stopped for any length of time needed as needed, such as for example, to further rotate and angularly orient the device. Secondary sleeve 210 and second primary sleeve 212 may retain some degree of overlap, and even when the coupling member 608 is fully disengaged from both sleeves, the two sleeves may remain adhered together by a dissolvable or temperature-activated adhesive that has not yet dissolved or that has not yet been temperature-deactivated. The rotational constraint between the second primary sleeve 212 and the catheter 228, and the rotational constraint between the two sleeves, ensure that further angular radial orientation of the device 100 remains possible through a torque of the end of the catheter 228 as indicated by "A." The previously disengaged first primary sleeve 530 may remain tethered to first coupling member 606 as illustrated for removal from the treatment site.

Figure 13:
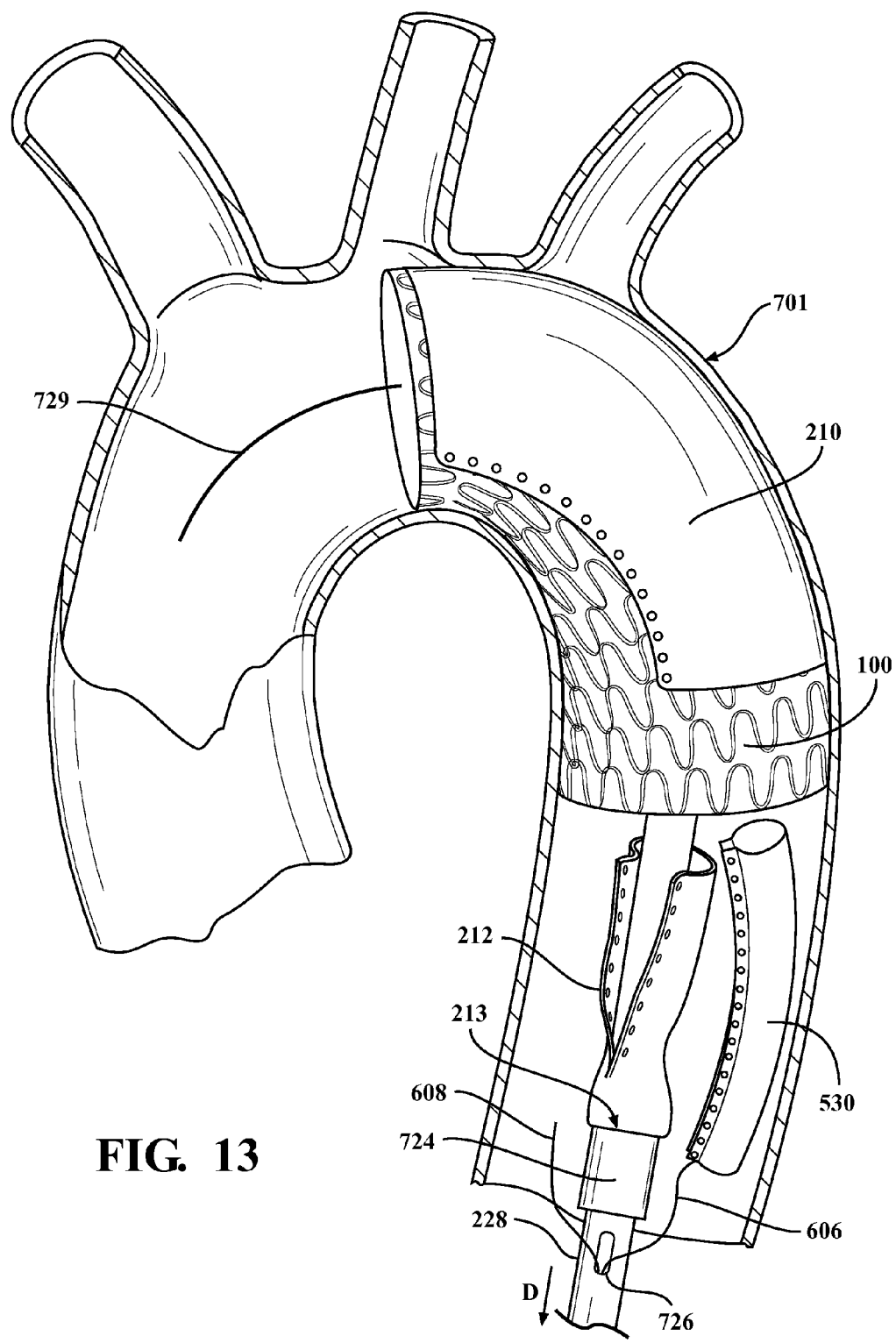

FIG. 13 illustrates the fully deployed and angularly oriented device 100 at the treatment site 701 in the patient. The secondary sleeve 210 is left behind. As discussed, the remaining secondary sleeve 210 can be left in the lumen at any rotational position required, for example by angular radial orientation prior to the release of the secondary sleeve 210. The second primary sleeve 212, affixed to the distal barrier 724 of catheter 228 at region 213, may be removed from the distal end of the device 100 by further withdrawal of the catheter 228 in direction "D." The previously disengaged first primary sleeve 530 may remain tethered to first coupling member 606 as illustrated for removal from the treatment site 701. The second coupling member 608 that previously weaved through and secured both the secondary sleeve 210 and the second primary sleeve 212 may be withdrawn into the portal 726 and out through a lumen disposed in the catheter 228. The remaining guide wire 729 can then be removed from the patient to complete the deployment and angular radial orientation procedure.

Figure 14:
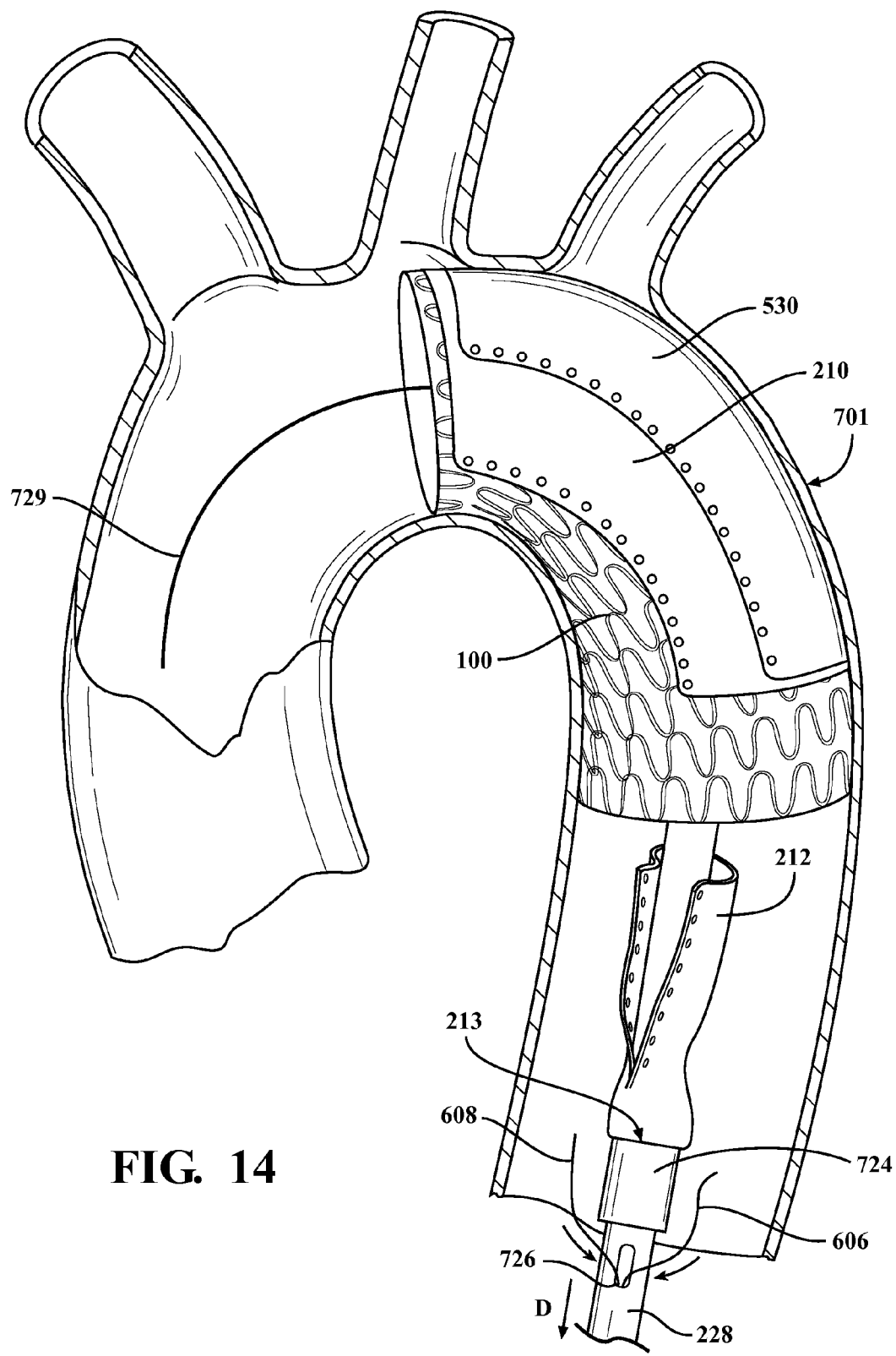

With reference now to FIG. 14, another embodiment of a fully deployed and angularly oriented device 100 at a treatment site 701 in a patient is illustrated. In this embodiment of the procedure, both the secondary sleeve 210 and the first primary sleeve 530 are left behind. The second primary sleeve 212, affixed to the distal barrier 724 of catheter 228 at region 213, may be removed from the distal end of the expanded device 100 by further withdrawal of the catheter 228 in direction "D." Both the first coupling member 606, previously used to secure the first primary sleeve 530, and the second coupling member 608, previously used to secure both the secondary sleeve 210 and the second primary sleeve 212, may be withdrawn into the portal 726 in the direction shown by the small arrows and out through a lumen disposed in the catheter 228. The remaining guide wire 729 can then be removed from the patient to complete the deployment and angular radial orientation procedure.

It will be apparent to those skilled in the art that various modifications and variations can be made in the present disclosure without departing from the spirit and scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An assembly comprising:
  a catheter;
  an expandable device disposed in a collapsed configuration at an end of the catheter;
  a first releasable sleeve coaxially covering a proximal portion of said expandable device; and
  a second releasable sleeve coaxially covering a distal portion of said expandable device, said second sleeve being rotatably constrained relative to the catheter,
  wherein said first sleeve overlaps a portion of said second sleeve and said first sleeve and second sleeve are rotatably constrained relative to each other.

2. The assembly of claim 1 wherein said first and second sleeves are rotatably constrained relative to each other by at least one of friction, dissolvable adhesive, temperature-activated adhesive and stitches.

3. The assembly of claim 1 wherein each of said first and second sleeves comprises a sheet of material wrapped circumferentially around said expandable device, with each sheet having a pair of substantially parallel and joinable opposing edges, and wherein each pair of opposing edges is releasably coupled into a releasable seam with at least one coupling member.

4. The assembly of claim 3 wherein both pairs of substantially parallel and joinable opposing edges are releasably coupled into one longitudinally contiguous releasable seam with only one coupling member.

5. The assembly of claim 3 wherein each pair of substantially parallel and joinable opposing edges are releasably coupled into a separate releasable seam with a distinct coupling member.

6. The assembly of claim 1 further comprising a secondary releasable sleeve covering said proximal portion of said expandable device, said secondary sleeve concentrically disposed underneath said first sleeve.

7. The assembly of claim 6 wherein said expandable device is disposed in a collapsed configuration on an end of said catheter with said second releasable sleeve affixed to and removable with said catheter.

8. The assembly of claim 1 wherein said expandable device comprises an endoluminal prosthesis.

9. The assembly of claim 1 wherein said expandable device is self-expanding.

10. The assembly of claim 1 wherein said expandable device is balloon-expandable.

11. A method for deploying an expandable device in a patient comprising:
    moving an assembly in the patient to a treatment site, said assembly comprising:
    a catheter; the expandable device disposed in a collapsed configuration at an end of the catheter; a first releasable sleeve coaxially covering a proximal portion of said expandable device; and a second releasable sleeve coaxially covering a distal portion of said expandable device, said second sleeve being rotatably constrained relative to the catheter, wherein said first sleeve overlaps a portion of said second sleeve and said first sleeve and second sleeve are rotatably constrained relative to each other;
    releasing said first sleeve;
    optionally expanding said proximal portion of said expandable device;
    rotating said catheter to cause rotation of said second sleeve to achieve a desired angular radial orientation of said expandable device;
    releasing said second sleeve; and
    optionally expanding unexpanded portions of said expandable device.

12. The method of claim 11 wherein said first and second sleeves are rotatably constrained relative to each other by at least one of friction, dissolvable adhesive, temperature-activated adhesive or stitching.

13. The method of claim 11 wherein each sleeve comprises a sheet of material wrapped circumferentially around said expandable device, with each sheet having a pair of substantially parallel and joinable opposing edges, and wherein each pair of opposing edges is releasably coupled into a releasable seam with at least one coupling member.

14. The method of claim 13 wherein both pairs of substantially parallel and joinable opposing edges are releasably coupled into one longitudinally contiguous releasable seam with only one coupling member.

15. The method of claim 13 further comprising the release of a secondary releasable sleeve, said secondary releasable sleeve covering said proximal portion of said expandable device and concentrically disposed underneath said first sleeve.

16. The method of claim 15 wherein said expandable device is disposed in a collapsed configuration on an end of said catheter with said second releasable sleeve irreversibly affixed to and removable with said catheter.

17. The method of claim 16 further comprising withdrawing said catheter from said patient after releasing said second sleeve, wherein said released second sleeve is removed from said patient with said catheter and wherein said first sleeve remains implanted in said patient with said expandable device.

18. The method of claim 11 wherein said expandable device comprises an endoluminal prosthesis.

19. The method of claim 11 wherein said expandable device is self-expanding.

20. The method of claim 11 wherein said expandable device is balloon-expandable.

* * * * *